United States Patent [19]
Bach et al.

[11] Patent Number: 5,804,738
[45] Date of Patent: Sep. 8, 1998

[54] METHOD AND APPARATUS FOR ON-LINE TESTING OF THE STIFFNESS OR STRENGTH OF PANELS AND ESPECIALLY OF WOOD PANELS

[75] Inventors: Lars Bach; Jung-June Cheng, both of Edmonton, Canada

[73] Assignee: Alberta Research Council, Edmonton, Canada

[21] Appl. No.: 747,680

[22] Filed: Nov. 12, 1996

[51] Int. Cl.[6] .................................................. G01N 3/20
[52] U.S. Cl. .............................................. 73/849; 73/852
[58] Field of Search .......................... 73/849, 852, 159, 73/854

[56] References Cited

U.S. PATENT DOCUMENTS

| | | | |
|---|---|---|---|
| 4,129,033 | 12/1978 | Otterbach | 73/852 |
| 4,589,288 | 5/1986 | Porter et al. | 73/852 |
| 4,708,020 | 11/1987 | Lau et al. | 73/852 |
| 4,852,029 | 7/1989 | Pope et al. | 73/852 |
| 4,991,432 | 2/1991 | Houghton et al. | 73/852 |
| 5,503,024 | 4/1996 | Bechtel et al. | 73/849 |

*Primary Examiner*—George Dombroske
*Assistant Examiner*—Max H. Noori
*Attorney, Agent, or Firm*—Neil Teitelbaum & Associates

[57] ABSTRACT

A method and apparatus for testing the stiffness or strength of wood panels while the panels are moving along a production line, in which the panels are moved lengthwise through a tester having lower rollers which are situated to support side or end marginal portions only of the panel while central upper rollers contacts a central region of the panel and subjects the panel to longitudinal or lateral bending. The forces corresponding to the bending are measured and used to obtain a measure of the stiffness or strength of the panel. Preferably, both a longitudinal and a lateral tester are provided, and each have two testing stations each applying a different amount of lateral bending, all of these amounts being in the substantially linear portion of the load deflection curve.

16 Claims, 3 Drawing Sheets

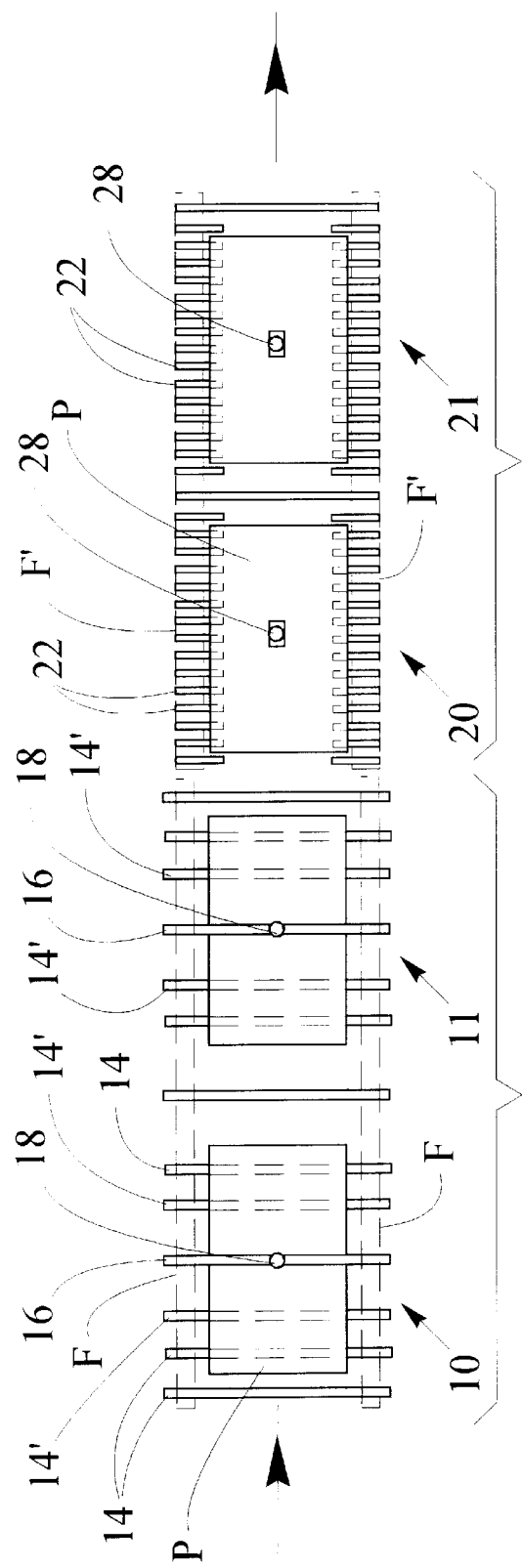
Fig. 1a
Fig. 1b
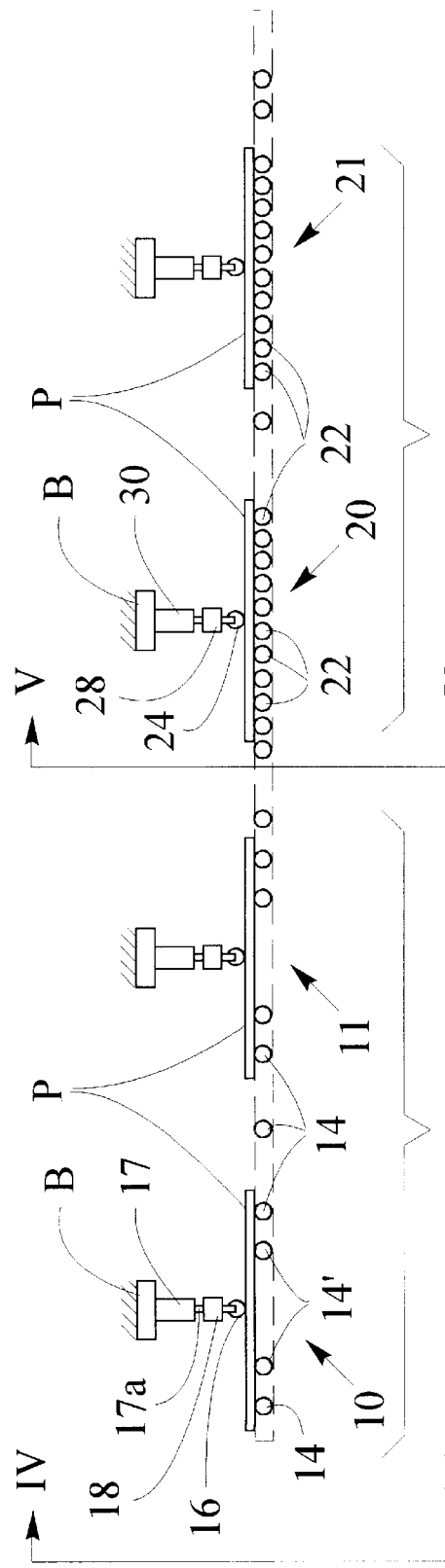
Fig. 2a
Fig. 2b

METHOD AND APPARATUS FOR ON-LINE TESTING OF THE STIFFNESS OR STRENGTH OF PANELS AND ESPECIALLY OF WOOD PANELS

BACKGROUND OF THE INVENTION

1. Field of the Invention

The present invention relates to methods and apparatus of non-destructive testing used in the production of panels, and especially wood panels and boards. The invention is particularly concerned with reconstituted panels, for example plywood, laminated veneer lumber, parallel strand lumber, flake board, hardboard, particle board, waferboard, oriented strand board (OSB), and the like. Such panels are typically made in sheets of 4 feet in width and 8 feet in length. The invention however may also be used for lumber such as wood planks, as well as panels of other materials such as wall panels containing cement or gypsum, and the term "panel" as used herein includes planks and sheets of glued lumber as well as reconstituted wood panels and panels of other materials.

2. Prior Art

In producing wood panels, and particularly OSB panels, it is desirable to monitor the stiffness of the board being produced; this is referred to as the machine stiffness rating or MSR. The stiffness (EI), or the modulus of elasticity (E or MOE) which can be derived from the stiffness, give good indications of the ultimate strength, or modulus of rupture (MOR), of the board. It may also be desired to impose a "proof" stress, similar to maximum design stress, on each board. Presently, stiffness testing or proof testing is usually done in static machines, and these require that a board be removed from the production line before it can be tested. It is desirable to have apparatus which can be placed in a production line so that the testing of boards can be done frequently or even continuously, as the panels move along the line, with little or no disruption of the line.

It has been proposed in U.S. Pat. No. 4,589,288, issued May 20, 1986, and of which one of the present inventors is co-inventor, to test the stiffness of a stationary panel in longitudinal bending by supporting the panel horizontally between transverse rollers under end margins of the panels, and applying downwards pressure by means of a bar applied transversely across the center of the panel, the bar extending parallel to the rollers and being positioned centrally between them as seen in plan view. To avoid problems with the fact that the load/deflection curve of a panel is non-linear at low loads, the pressure is applied in two stages, and a measurement is taken of the deflection at each stage. The loads applied at these stages are chosen so that they are in the substantially linear portion of the load deflection curve. While this apparatus is useful, it does not allow a board to continue moving in the usual line during the testing, and it is also limited in that it only measures the stiffness in the longitudinal (or "parallel" direction). It is desirable to be able to measure the stiffness in the width-wise direction, which may also be referred to as the transverse, lateral, or "perpendicular" direction as well as the longitudinal direction, since properties of the panel may not be uniform in all directions. This is not convenient with the apparatus of the aforesaid patent, since this would require the use of a bar and rollers longer than the panel, i.e. more than 8 ft. in length for 4 by 8 ft. panels.

Also, it is desirable that a measure can be obtained of stiffness near the edges of a panel, since edge stiffness is particularly desirable for some end uses.

Other prior art includes testing apparatus for lumber or panels which bends this longitudinally into an S-shaped curve as it passes along a production line, and measures the bending force. An example of a panel tester of this kind is shown in U.S. Pat. No. 4,708,020, which issued Nov. 24, 1987, to Lau et al. Although bending occurs in two stages, it seems that the degree of bending in each stage would be similar. For panels, the prior art also includes apparatus which makes use of vibrations or shock waves in the wood caused by impact devices. However, the latter type of apparatus can only operate on stationary panels, and not on panels which are moving along a production line.

The present invention provides apparatus which, in its preferred form, can measure the width-wise stiffness of a panel, also referred to herein as the transverse or lateral stiffness of the panel, and preferably also the longitudinal stiffness, and does both measurements while the panel is moving along the usual production line. The apparatus can also be used for measuring proof strength.

SUMMARY OF THE INVENTION

In accordance with one aspect of the present invention, a method for testing the stiffness or strength of panels comprises moving a panel lengthwise through a lateral (or "with-wise" or "transverse") tester having spaced, normally lower, rotary means which are situated to contact side portions only of one face of the panel while central, normally upper, rotary means contacts and deflects a laterally central region of the other face of the panel and deflects the panel to cause lateral bending, and simultaneously measuring the force corresponding to the lateral bending; and using the force measurements along with deflection data related to bending to obtain a measure of the stiffness or strength of the panel.

Since the longitudinal properties also need to be tested, preferably on the production line, the invention will usually also include the step of moving the panel lengthwise through a longitudinal tester having spaced, normally lower, rotary means which are situated to contact end portions only of one face of the panel while central, normally upper, rotary means contacts a longitudinally central region of the other face of the panel and deflects the panel to cause longitudinal bending as it moves through the tester, and simultaneously measuring the force corresponding to the longitudinal bending. This longitudinal testing step can be done before or after the lateral testing.

As mentioned, in aforesaid U.S. Pat. No. 4,589,288 the bending force is applied in two stages, and measurements are taken of the force and deflection at each stage, so that the testing can be confined to the linear portion of the load deflection curve for the panel. In the present invention, it is also desirable for stiffness measurements that the force/deflection measurements be done in two stages. Accordingly, each of the lateral and longitudinal testers may have two testing stations, each station of the longitudinal tester applying a different amount of longitudinal bending, and each station of the lateral tester applying a different amount of lateral bending, all of the amounts of bending being within the substantially linear portion of the load/deflection curve, the longitudinal and lateral stiffness being determined by comparing the various bending forces with the corresponding deflections. Unlike in the aforesaid Lau et al. patent, the amounts of bending applied in the two similar stations (longitudinal or lateral) are significantly different, with one of the stations applying more than twice the amount of bending as the other similar station.

The longitudinal tester may have a transverse roller applying a force substantially evenly across the panel. Alternatively, a series of pressure applying devices may be distributed across the center of the panel, and separate readings taken of the deflections at different lateral positions, to give a comparison between edge stiffness and stiffness at the center of the panel. Longitudinal stiffness near to the edges of a panel is of interest in relation to the suitability of panels for flooring and roofing.

The invention also includes apparatus for testing the stiffness of a panel comprising a lateral tester having spaced, normally lower, rotary means which are situated to contact side portions only of one face of the panel and having laterally central, normally upper, rotary means which contacts a central region of the other face of the panel and deflects the panel to cause a lateral bending of the panel as it moves through the tester. The tester has load sensing means which sense the force being applied to the central rotary means by reason of the bending, whereby the stiffness or strength of the panel may be determined by comparing the forces produced in bending to the amount of the deflection related to the bending.

BRIEF DESCRIPTION OF THE DRAWINGS

Preferred embodiments of the invention will now be described by way of example with reference to the accompanying drawings, in which;

FIG. 1a is a diagrammatic plan view of first and second testing stations of a longitudinal stiffness tester for testing a panel while it moves along a production line;

FIG. 1b is a diagrammatic plan view of first and second testing stations of a lateral stiffness tester for testing a panel as it moves along the line;

FIG. 2a is a side view of the longitudinal stiffness tester;

FIG. 2b is a side view of the lateral stiffness tester;

FIG. 3 is an enlarged side view of a mount for the pressure rollers shown in FIG. 2a;

FIG. 4 is a frontal view of a pressure roller and mount for the longitudinal tester, taken on lines 4—4 of FIG. 2a;

DETAILED DESCRIPTION

FIGS. 1a and 2a show a longitudinal stiffness tester which has first and second testing stations 10 and 11 respectively, suitable for testing the stiffness of wood panels P as they move along a production line at normal production line speed of 50 to 200 ft/min. The stations are similar, each having a series of lower transverse rollers 14, held by side frame members indicated at F in broken lines, and which support the lower face of each panel P. These rollers include a pair of transverse pressure rollers 14' which are spaced apart, longitudinally of the production line, by a distance less than the 8 foot length of the panels and more than ¼ the length of the panels. The optimum spacing of rollers 14' depends on the amount of deflection desired and the thickness of the panels. Each station also has a central, upper transverse roller 16 parallel to and situated midway between the lower spaced rollers, when seen in plan view, and which contacts the top face of the panel and deflects the center of the panel passing through the station. The lower rollers 14 and 14' are set at the same height, and the upper roller 16 has its height set so that the panel is bent longitudinally by predetermined amounts, usually in the range of 0.1 to 1.5 inches; this is determined by stress considerations, as discussed below.

Figure 3:
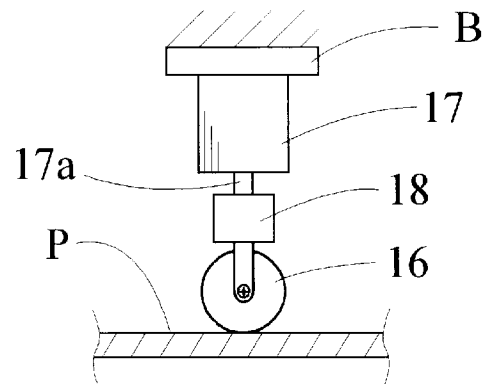
Figure 4:
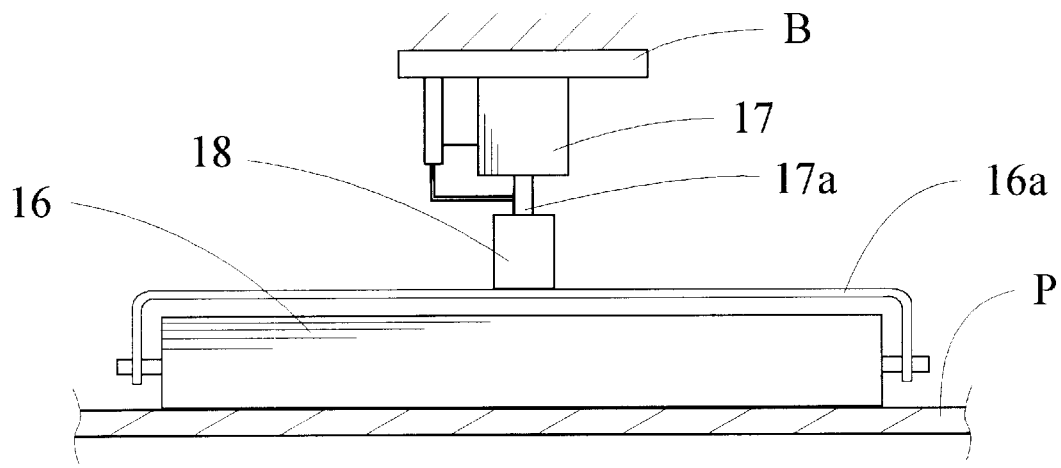

Referring to FIGS. 3 and 4, the mounting for each upper roller 16 incorporates a programmable hydraulic cylinder 17 with ram 17a, the ram being connected to the roller holding bracket 16a via a load cell 18. The ram is also connected to a deflectometer 19, which serves as a programmable hydraulic position controller, and which controls the upper roller height and gives a measurement of the deflection produced on the panel by the upper roller. The upper end of the cylinder 17 is carried by a support beam B. The hydraulic controllers and load cells are connected to monitoring computer means, e.g. a programmable logic controller (PLC), which gives a continuous indication of the bending load to which each upper roller is subjected, and the corresponding deflections. Since there are gaps between the panels, and the speed of movement of the panels is reasonably uniform, the computer can be programmed to detect when the load cell is measuring a load corresponding to the longitudinal central portion of the panel. Alternatively, one may choose merely to measure the highest load given by each panel.

To ensure that leading edges of the panels are not struck by the rollers 16, the PLC circuit controlling the cylinder 17 includes a photo-electric cell effective to lift the roller whenever it senses the gap between adjacent panels, and which brings the roller into contact with a panel only when this is supported on the two pressure rollers 14'.

The deflections of the panels in each of the stations are chosen so as to be on the substantially linear portion of the load deflection curve. Knowing the difference in deflection given by the two stations, and having measurements of the corresponding bending forces, the longitudinal stiffness of the panels can be calculated.

Figure 5:
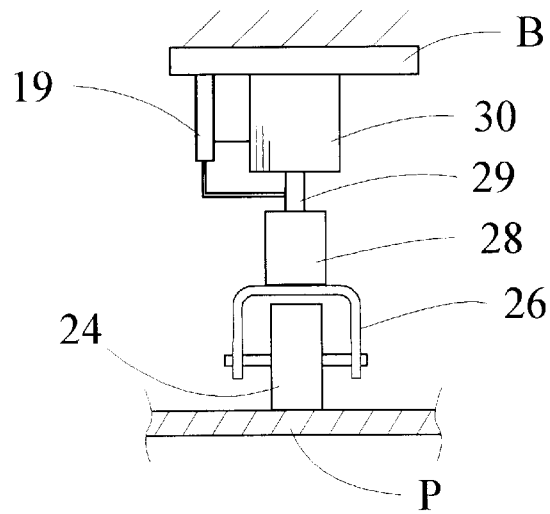
FIG. 5 is a frontal view of a pressure wheel used in the lateral stiffness tester station, taken along lines 5—5 of FIG. 2b.

Turning now to the lateral or width-wise stiffness tester shown in FIGS. 1b and 2b, again this comprises two stations, indicated at 20 and 21, which are similar to each other except for the amount of bending produced. Each station has two sets of lower rollers 22 which are short, are supported in cantilever manner from frame parts F', and contact only the outer side margins of the lower face of the panel; for example each set of rollers may support say 2 to 3 inches of a 4 foot wide panel, or less than $\frac{1}{10}$ the width of the panel. In the lateral and longitudinal center of each station is a wheel-like roller 24 which contacts the upper face of each panel and applies pressure to and deflects the center of the panel as it passes through the station. The nature of this roller 24 is shown in end view, with its mounting, in FIG. 5; in side view the mounting is the same as that for roller 16 shown in FIG. 3. As shown in FIG. 5, the roller 24 is carried by an axle 25 held by a bracket 26 mounted on a load cell 28. The load cell is mounted on the lower end of a ram 29 projecting from a programmable hydraulic cylinder 30, the cylinder having its upper end fixed to cross beam B. Also joining the ram to the beam is a deflectometer 29, similar to deflectometer 19 described above. All these items operate in the same manner as the corresponding items in the longitudinal tester, and allow both loads and deflections to be monitored as panels pass through the tester. The panels are moved by driving at least some of rollers 14 and 14'.

The load cells and the deflectometers are both connected into a computer which compares the loads produced by the first deflection in the first station to the second deflection in the second station to give an indication of lateral stiffness.

For both the longitudinal tester, the amount of bending at the first station is chosen to be equivalent to a stress of 200 to 300 psi., or about 5–10% of the maximum stress which the panel can be expected to withstand in the longitudinal direction, and the deflection at the second station is equivalent to a stress of about 1,000 to 1,200 psi, or about 30% of this maximum stress. For the lateral tester, again the first and second stations exert stresses of about 10% and 30% of the maximum lateral stress, although this maximum lateral stress is much lower than the maximum stress in the longitudinal direction. Thus the amount of bending produced in the second station is at least twice, and preferably about three times, the amount of stress produced in the first station. Naturally, the setting of the upper roller will also depend on the thickness of the panels. Altogether, the hydraulic cylinders 17 and 30 will require a stroke of a very few inches. In setting up the apparatus, the hydraulic cylinder settings are made with a stationary panel P in the central position in each of the stations, i.e. with the upper rollers contacting the longitudinal centers of the panels. Upon start-up, data from all four rollers is collected for each 4 inches of longitudinal movement of each panel.

It may be noted that while the longitudinal stiffness tester has line loading along the lateral center and thus produces pure longitudinal bending, the lateral stiffness tester, which applies substantially point loading at the center of the panel, might be considered likely to produce a compound bending, i.e. some longitudinal bending as well as lateral bending. However, it has been found in tests that with the side margins of the panel supported generally in the manner shown, a load applied centrally on a small area of a panel produces a load deflection curve very close to that produced by applying a line load along the center. Instead of a roller, a wheel or near spherical roller ball could be used, and the term "rotary means" is intended to cover such alternatives.

Figure 6:
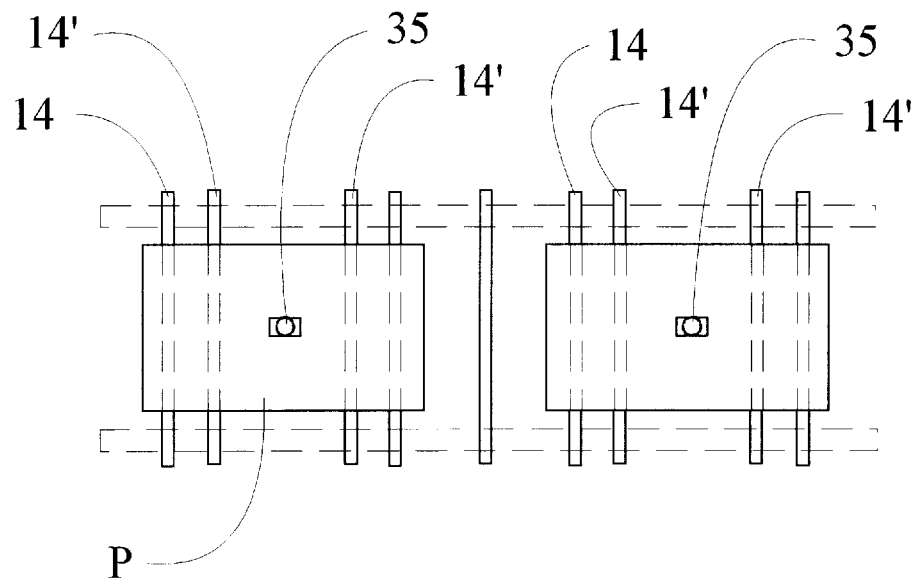
FIG. 6 is a plan view of a modified longitudinal stiffness tester having a pressure wheel in place of a roller.

FIG. 6 shows a simplification of the longitudinal stiffness tester in which the transverse roller of each station is replaced by a single central wheel-type roller 35. It has been found that this produces bending very similar to that produced by the transverse roller, and produces similar results for longitudinal stiffness or proof stress.

Figure 7:
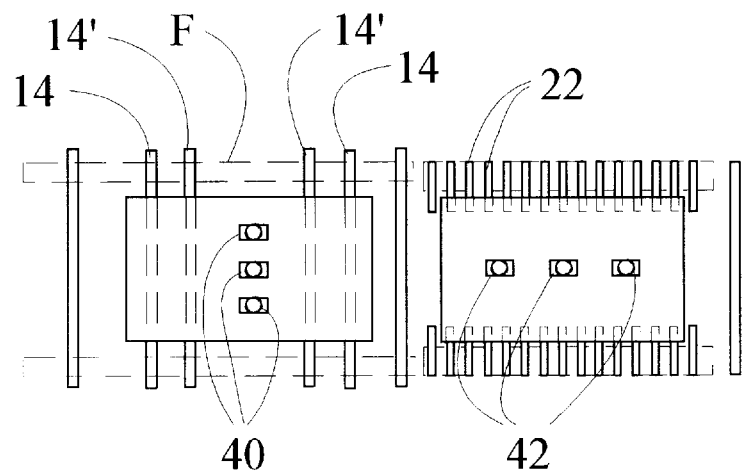
FIG. 7 is a plan view of modified longitudinal and lateral stiffness testing stations having several pressure wheels in different arrangements.

FIG. 7 shows further variations of one station of the longitudinal tester and one station of the lateral tester, in which, for each station, instead of using a transverse roller 16 or a single wheel, several wheels or wheel-like rollers 40, 42, each similar to roller 24 and having similar mountings, are used. In the longitudinal testing station, three wheels 40 are used, spaced transversely across the station. Each is separately connected to a load cell and deflectometer, allowing a measure of longitudinal stiffness to be obtained at different positions across the panel, including near the edges of the panel. In the lateral testing station, three wheels 42 are used, spaced longitudinally along the centerline of the panel.

The above description refers to setting the positions of the pressure rollers or wheels and measuring the pressures produced, i.e. using fixed deflection and variable pressure. However, it is also possible to use relatively fixed pressure and to measure the variable deflections with the deflectometers.

Furthermore, instead of merely measuring stiffness, which is done with bending loads well below the maximum load a panel can be expected to bear, a higher loading, i.e. a "proof" load, may be used, similar to the maximum design load for the panel, the panels being monitored to see if such loading produces any permanent structural change. For this purpose, it is not necessary that there be two stages of measurements using different loads.

We claim:

1. A method for testing the width-wise stiffness or strength of panels, comprising moving a panel lengthwise through a width-wise tester having spaced rotary means which are situated to contact side portions only of one face of the panel while central rotary means contacts a laterally central region of the other face of the panel and deflects the panel to cause bending across the panel width, measuring the force corresponding to the width-wise bending; and using the force measurements along with deflection data relating to the bending to obtain a measure of the width-wise stiffness or strength of the panel.

2. A method according to claim 1, wherein said width-wise tester has two testing stations, one of said stations applying an amount of width-wise bending which is in the same direction and at least twice the amount of the width-wise bending applied by the other said station, said amounts of bending being in the substantially linear portion of the load deflection curve for the panel, the width-wise stiffness being determined by comparing the bending forces and the corresponding deflections produced by the bending forces in the each station.

3. A method for testing the stiffness or strength of panels, comprising the steps of:

a) moving a panel lengthwise through a longitudinal tester having spaced rotary means which are situated to contact end portions only of one face of the panel while central rotary means contacts a longitudinally central region of the other face of the panel and deflects the panel to cause longitudinal bending as it moves through said tester, and measuring the force corresponding to said longitudinal bending;

b) moving the panel lengthwise through a width-wise tester having rotary means which are situated to contact side portions only of one face of the panel while central rotary means contacts a laterally central region of the other face of the panel and deflects the panel to cause width-wise bending, and measuring the force corresponding to said width-wise bending; and using the force and deflection data relating to said bending in each station to obtain a measure of the stiffness or strength of the panel.

4. A method according to claim 3, wherein each of said testers has two testing stations, one station of the longitudinal tester applying an amount of longitudinal bending which is in the same direction as and at least twice as much as the other station of the same longitudinal tester, and each station of the width-wise tester applying an amount of width-wise bending which is in the same direction as and at least twice as much as the other station of the same width-wise tester, all of said amounts of bending being in the substantially linear portion of the load deflection curve for the panel, the longitudinal and lateral stiffness being determined by comparing the bending forces with the corresponding deflections for the various stations.

5. Apparatus for testing the stiffness of a panel in longitudinal or width-wise bending as it passes longitudinally through the apparatus, comprising:

a first testing station having upper and lower rotary means, one of said upper or lower rotary means being positioned sufficiently apart to contact outer portions only of one face of the panel when the other rotary means is in contact with a central region of the other face of the panel, said upper and lower rotary means also being situated so that a panel is bent to a first degree when passing through said section;

a second testing station having further upper and lower rotary means, one of said further upper or lower rotary means being also positioned sufficiently apart to contact outer portions only of said one face of the panel when the other further rotary means is in contact with a central region of said other face of the panel, said further upper and lower rotary means also being situated so that a panel is bent to a second degree when passing through said section, said second degree of bending being in the same direction as and at least twice as much as said first degree of bending;

each said testing station section having load sensing means which senses the force applied to the rotary means by reason of said bending, whereby the stiffness of the panel is determinable by comparing the force applied in bending to the deflections produced in said first and second degrees of bending.

6. Apparatus according to claim 5, wherein said lower and upper rotary means and said further lower and upper rotary means include, for each station, a spaced pair of lower rollers and a single upper roller all extending transversely of the panel, the upper roller being positioned centrally between the lower rollers when seen in plan view, and so that a panel passing between said rollers is bent longitudinally.

7. A method according to claim 3, wherein said force and deflection data are monitored as the panel passes through each tester to indicate an output corresponding to the bending force when a panel center is adjacent the central rotary means.

8. A method for testing the stiffness of panels, comprising the steps of:

moving a panel lengthwise through a first testing station having spaced rotary means which are situated to contact outer portions only of one face of the panel while central rotary means contacts a central region of the other face of the panel and deflects the panel to a first degree to cause a first degree of bending as it moves through the station, and measuring the forces corresponding to said first degree of bending;

subsequently moving the panel lengthwise through a second similar testing station also having spaced rotary means which are situated to contact outer portions only of one face of the panel while central rotary means contacts a central region of the other face of the panel and deflects the panel to a second degree to cause a second degree of bending which is in the same direction as and at least twice as great as the first degree of bending as it moves through the second station, and measuring the forces corresponding to said second degree of bending;

comparing the forces to produce said first and second degree of bending with said first and second degrees of deflection to obtain a measure of the stiffness of the panel, all of said degrees of bending being in the substantially linear portion of the load deflection curve.

9. A method according to claim 8, wherein, for each station, said spaced rotary means include a pair of lower rollers spaced to support outer end portions only of the panel, and said central rotary means is a single upper roller positioned centrally between the lower rollers when seen in plan view, so that a panel passing between said rollers is bent longitudinally.

10. Apparatus according to claim 5, wherein said lower rotary means and said further lower rotary means are positioned to support side margins only of the panels, and wherein the upper rotary means and further upper rotary means are situated at a lateral center between said lower rotary means and further lower rotary means, so that a panel passing between the rotary means is bent across the panel width.

11. A method according to claim 8, wherein said force at the center of the panel is monitored as the panel passes through each testing station to produce an output corresponding to the bending force when a panel center is adjacent the central rotary means.

12. A method according to claim 1, wherein said force is a proof load.

13. A method according to claim 3, wherein said forces applied in the longitudinal and lateral testers are proof loads.

14. Apparatus for testing the width-wise strength or stiffness of a panel while the panel moves longitudinally through the apparatus, comprising a width-wise tester having spaced rotary means which are situated to contact side portions only of one face of the panel and having laterally central rotary means which contacts a central region of the other face of the panel and deflects the panel to cause a bending across the panel width of the panel as it moves through the tester, whereby the stiffness or strength of the panel is determinable by comparing the forces and deflection produced in said bending.

15. Apparatus for testing the stiffness or strength of a panel while the panel moves longitudinally through the apparatus, comprising:

a longitudinal tester having spaced rotary means which are situated to contact end portions only of one face of the panel and having longitudinally central rotary means which contacts a central region of the other face of the panel and deflects the panel to cause longitudinal bending of the panel as it moves through said tester, a width-wise tester having spaced rotary means which are situated to contact side portions only of one face of the panel and having laterally central rotary means which contacts a central region of the other face of the panel and deflects the panel to cause a bending across the width of the panel as it moves through the tester, each said tester having load sensing means which senses force applied to the rotary means by reason of said bending, whereby the stiffness or strength of the panel is determinable by comparing the forces and deflections produced in bending.

16. Apparatus according to claim 15, wherein said longitudinal tester has said longitudinally central rotary means in the form of rollers spaced across the panel and each connected to a separate load sensor, whereby an indication can be obtained of the edge stiffness of the panel.

* * * * *